US 6,652,870 B2

(12) United States Patent
Campbell et al.

(10) Patent No.: US 6,652,870 B2
(45) Date of Patent: Nov. 25, 2003

(54) WILDLIFE CONTROLLANT AND METHODS OF USING THE SAME

(76) Inventors: Dan L. Campbell, 5227 Gifford Rd. SW., Olympia, WA (US) 98512; Joanne M. Campbell, 5227 Gifford Rd. SW., Olympia, WA (US) 98512; Clinton L. Campbell, 5227 Gifford Rd. SW., Olympia, WA (US) 98512

( * ) Notice: Subject to any disclaimer, the term of this patent is extended or adjusted under 35 U.S.C. 154(b) by 0 days.

(21) Appl. No.: 09/991,113

(22) Filed: Nov. 15, 2001

(65) Prior Publication Data

US 2002/0155143 A1 Oct. 24, 2002

Related U.S. Application Data

(60) Provisional application No. 60/285,537, filed on Apr. 23, 2001.

(51) Int. Cl.[7] .......................... A01N 25/32; A01N 25/34
(52) U.S. Cl. ....................... 424/406; 424/405; 424/407; 424/410; 424/411; 514/920
(58) Field of Search .......................... 424/410, 84, 417, 424/418, 421, 406, 407, 411, 715, 602, 405; 514/920, 953

(56) References Cited

U.S. PATENT DOCUMENTS

| | | | | |
|---|---|---|---|---|
| 4,447,421 A | * | 5/1984 | Klothen | 424/227 |
| 4,505,936 A | * | 3/1985 | Meyers et al. | 426/1 |

OTHER PUBLICATIONS

Campbell, D.L., Guidelines for Field Evaluations of Repellents to Control Deer Damage to Reforestation, Special Technical Publication of American Society for Testing and Materials, vol. 625, 1977.

Bullard, Roger W., Preparation and Evaluation of a Synthetic Fermented Egg Coyote Attractant and Deer Repellent, J. Agric. Food Chem., vol. 26, No. 1, 1978.

Campbell, Dan L., Deer Repelled from Douglas Fir New Growth Using BGR–P and Aversive Conditioning, Department of Natural Resources Note, No. 46, Oct. 22, 1987.

Campbell, Dan L., Recent Approaches to Controlling Mountain Beavers in Pacific Northwest Forests, Denver Wildlife Research Center, Printed at Univ. of Calif., Davis 13: 183–187, 1988.

* cited by examiner

Primary Examiner—Neil S. Levy
(74) Attorney, Agent, or Firm—Ingrid McTaggart

(57) ABSTRACT

An animal controllant comprises a shellfish waste material mixed with a binding agent and applied to plants such that the controllant repels or attracts animals therefrom, depending on the animal desired to be controlled. The shellfish waste material typically comprises shell and/or tissue material of crab, lobster, mussel, shrimp, clam, oyster, and mixtures thereof, and the binding agent typically comprises clay, corn oil and/or ground corn. A colorant such as alfalfa, which may also act as a binder, may also be added to the controllant formulation. The controllant may be applied to plants by itself or with the aid of an adhesive. The repellent may also be applied to a substrate such as a flag or a protective tube, which is then positioned on or about the plant. The inventive shellfish waste formulation has been found to protect plants by repelling animals including deer, elk, hares, rabbits, gophers, voles, mountain beavers, and moles and by attracting certain insectivorous and carnivorous animals, such as dogs, wolves and coyotes. The controllant is believed to function by releasing ammonia as the formulation decomposes as a result of exposure to sunlight and water.

2 Claims, 3 Drawing Sheets

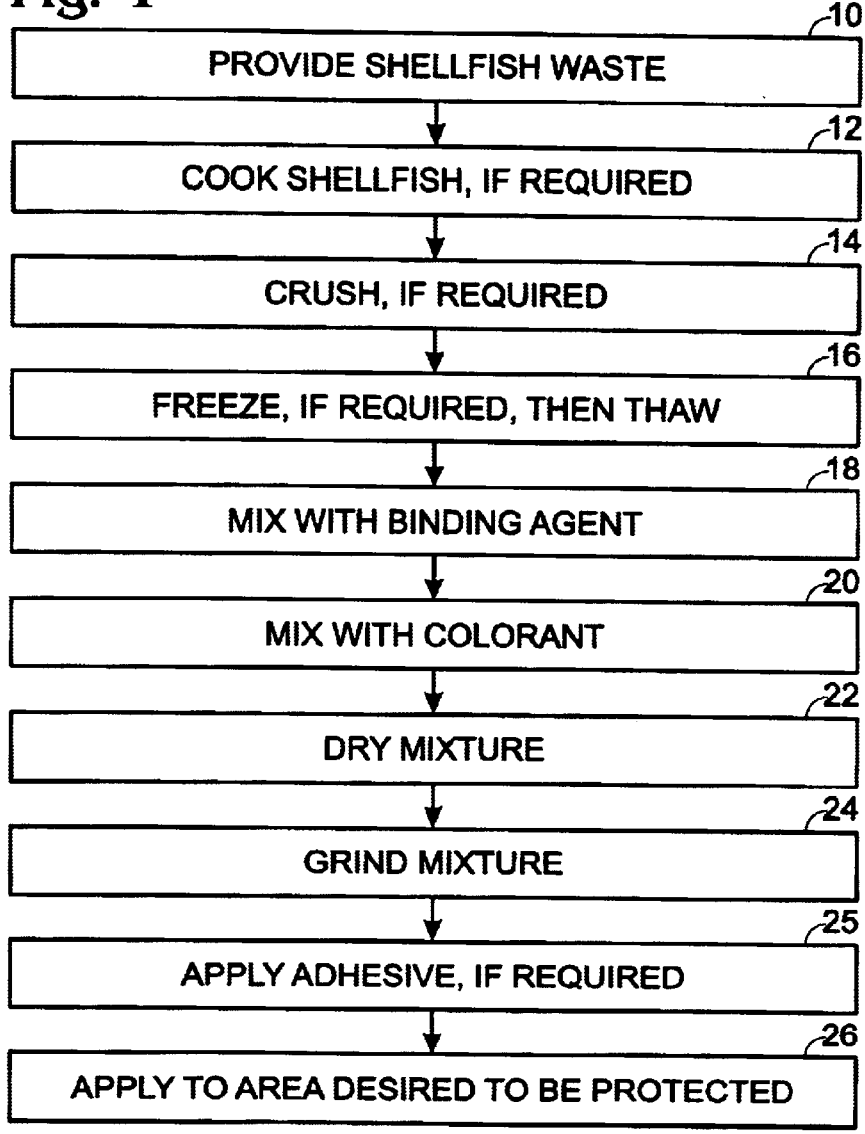
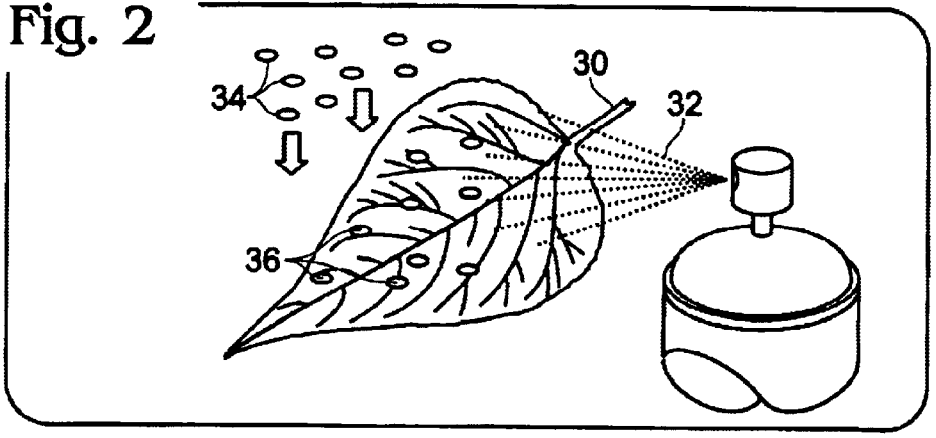

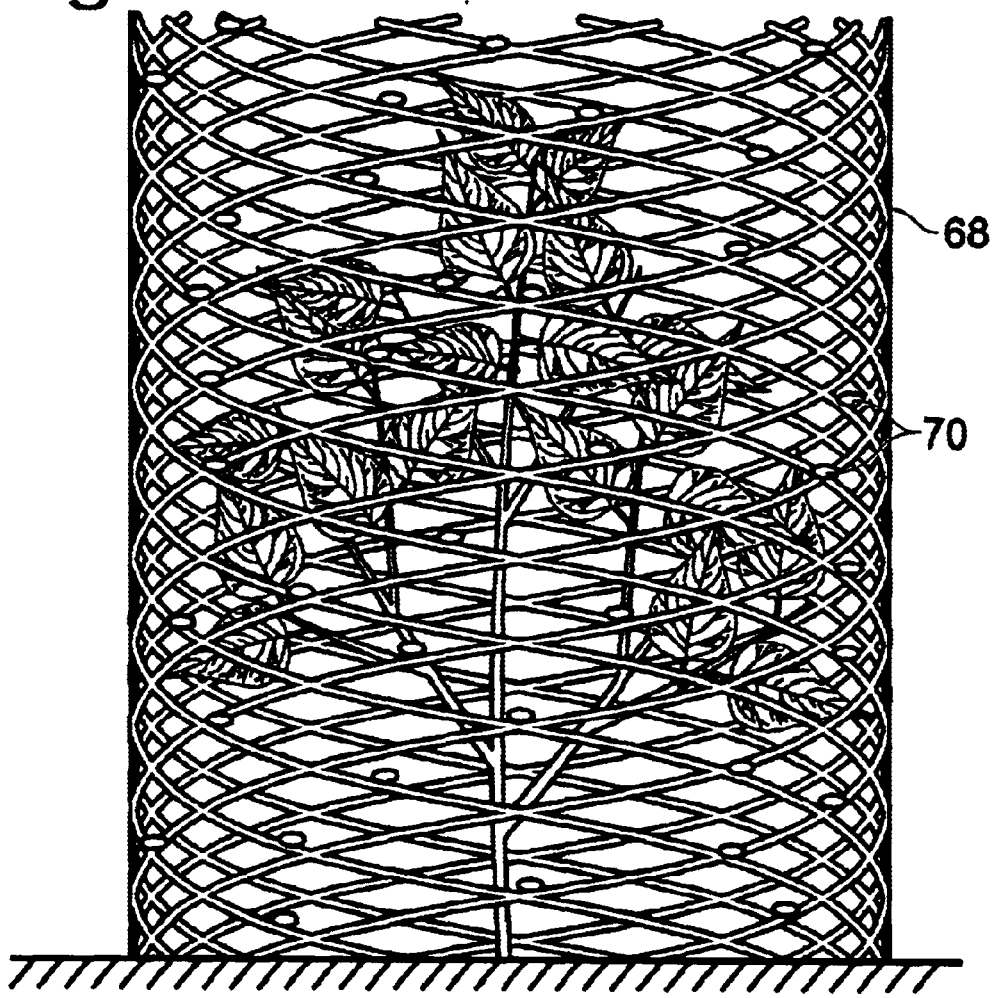

WILDLIFE CONTROLLANT AND METHODS OF USING THE SAME

PRIORITY

The present patent application claims priority on an earlier filed U.S. provisional patent application, filed Apr. 23, 2001, entitled Wildlife Repellent and Attractant from Mussel Waste, having Ser. No. 60/285,537.

FIELD OF THE INVENTION

The present invention relates to wildlife controllants and methods of using the same and, more particularly, to wildlife controllants including shellfish waste therein.

BACKGROUND OF THE INVENTION

Deer, elk and other wildlife species are often responsible for a variety of feeding injuries to forest crops, ornamental plants, and food crops. Few non-lethal methods, other than exclusion by barriers, are presently available to prevent or control damage to these crops by such wildlife species. Most repellent materials available, if effective, are short lived in effectiveness and are often difficult to effectively adhere to wet plants, during wet weather, or when crops are irrigated. The present invention provides an alternative to barriers, or can increase the effectiveness of barriers, by providing an improved wildlife controllant to protect plants.

Moles and some burrowing rodents excavate soil into mounds in lawns, gardens, and crop fields where mounds are not wanted. The excavation caused by these animals may cause injury to persons, damage to machinery and may damage certain crops. These animals also construct underground tunnels that allow voles or other rodents to invade and further damage crops. Kill trapping has been the preferred control method. Trapping, however, has been banned in certain states such as in Washington state. The present invention and the described application may be used as an animal controllant designed to cause burrows and nests to be abandoned by moles and certain rodents, thereby reducing or eliminating further burrowing and soil excavation activity.

U.S. Pat. Nos. 4,965,070 and 5,183,661 describe, respectively; (1) a deer repellent formulation of thiram, chicken eggs, liquid hot sauce, and adhesive, and (2) the deer repellent formulation described above, supported by a medium utilizing a cotton and polyester support rope wrapped on or among plants, and a support medium of clay material for application under and around plants. Thiram, however, is now seldom used as a plant repellent if there is a chance of ingestion by humans. This is because of a possible severe physiological reaction to the thiram. Also, chicken eggs and hot pepper sauce usually have little repellency at low concentrations. The rope support medium for deer repellent described in these prior art disclosures is intended as a barrier. However, deer and elk usually easily cross such "barriers" to examine plants they intend to browse. Moreover, the clay support medium for deer repellent described in this prior art typically is distributed under or around shrubs and plants, instead of on foliage, where it is most effective.

U.S. Pat. No. 5,013,551 describes the incorporation of various terpenes and concentrations of terpenes into linear, low-density polyethylene (LLDPE) for forming trash bags resistant to attack by a wide variety of animals. However, the terpenes described do not function as a repellent to ungulates such as deer or elk. Moreover, this prior art reference does not teach a method of repelling animals from browsing foliage.

U.S. Pat. No. 3,962,425 describes a ruminant repellent composition applied in a non-phytotoxic amount to discourage browsing of edible material. This prior art reference consists of lipodal material, such as whole salmon, admixed with a lipolytic enzyme, with the effectiveness increased by adding other lipoidal material, to form a repellent putrescent decomposition product. The lipoidal product described, including the addition of lipoidal enzymes, is generally not stable and readily decomposes, thereby limiting the effective life of the product.

U.S. Pat. No. 5,356,881 describes wildlife repellent products derived from plant species to protect plants and other targets against damage from a variety of animal species. However, this prior art reference does not disclose a product that protects plants from ruminants.

SUMMARY OF THE INVENTION

The present invention describes the use and manufacture of animal controllant formulations made from the clean waste and shells of crustaceans and other shellfish, such as crabs, lobsters, mussels, shrimp, clams, oysters, and the like, and methods of application of these controllant formulations to forest, ornamental, and other plants to protect them from damage by animals including ruminants such as deer and elk. The formulation may also be placed at excavation sites to discourage the presence of burrowing animals or as an attractant which allows the safe and humane trapping of nuisance animals. Accordingly, by the term "controllant" applicants mean that the shellfish waste and shell formulations described herein can be utilized as both animal repellents and as animal attractants, depending on the animals desired to be controlled.

The inventive formulations and methods utilize waste products from the shellfish industry, specifically those waste products from the processing of crustaceans for human food. The shellfish waste products typically are used for the purpose of applying them to plants needing protection from feeding injuries caused by wildlife and domestic animals. The inventive shellfish waste formulations and methods include different product formulating techniques and different application techniques. Some of these approaches include: application of shellfish waste to the root zones of plants to repel animals; application of the repellent shellfish waste or waste extractions formulated within a liquid carrier or paint substrate to be sprayed on foliage in wet or dry weather; application of shellfish waste to food crops for repelling animals; use of shellfish waste to protect plants against certain rodents such as mountain beavers and pocket gophers; use of shellfish waste as bird repellents; use of the shellfish waste on plastic tape which may be secured to foliage limbs; use of shellfish waste formed with a waterproof adhesive for use as fishing lures; and use of shellfish waste as an attractant for control of damage activities of certain mammalian insectivores. The inventive formulation may also be used as a plant nutrient.

Accordingly, it is an object of the present invention to provide a reliable non-toxic natural occurring controllant material which can be applied to a variety of plant species to protect them from feeding injuries by a variety of animals, including deer, elk, hare, rabbits, certain burrowing rodents such as pocket gophers, mountain beavers, and voles, and carnivores such as coyotes, wolves and dogs.

A further object of the invention is to provide a long lasting, aesthetically acceptable, and easily applied, non-phytotoxic controllant which can be applied during dry or wet weather conditions.

Another object of the present invention is to use non-phytotoxic tree marking paint, or the adhesive components of tree marking paint, to enable application of the controllant to plant foliage and adhesion of the controllant during rain or irrigation.

Still another object of the present invention is to utilize or increase utilization of a waste by-product of the seafood industry as an easily formulated and relatively inexpensive controllant material.

Yet another object of the present invention is to use granular clay, such as bentonite clay, to adsorb and absorb liquids from previously frozen shellfish waste material, to bind and stabilize the waste materials while they are being processed and dried.

Still a further object of the present invention is to provide a shellfish waste formulation that has limited proteolytic activity, if any, while the formulation is being processed and dried.

Another object of the present invention is to use granular clay as an inert extender for a shellfish waste formulation.

Yet another object of the present invention is to use a shellfish waste controllant on tape flags to attach to plants, as a signal to animals such as deer and elk that the plants are unpalatable.

A further object of the present invention is to utilize or recycle used computer tape as a relatively inexpensive carrier for a controllant material.

Another object of the present invention is to provide a controllant for use in a burrow treatment to control burrowing and soil excavation activity of moles, pocket gophers, mountain beavers, and voles.

Yet another object of the present invention is to use corn oil, dry ground corn and alfalfa to adsorb and absorb liquids from shellfish waste, to bind and stabilize the material while being processed and dried, and to limit proteolysis, if any, while being processed and dried, and as an inert extender for improving controllant properties.

An additional object of the present invention is to use corn oil and/or ground corn in combination with cooked shellfish waste to aid in the controlled release of components causing repellent or attractant properties, to cause repellency or attraction, and to improve adhesion of the controllant material.

The primary advantages of the present invention include the utilization of former shellfish waste, such as the meat and shell of the shellfish, with or without combination in a bentonite or similar clay matrix, as a safe and effective, non-toxic natural formulation which is non-phytotoxic, as a controllant for deer and elk. This long lasting controllant can be applied to wet or dry plant foliage using suitable adhesives, or can be applied as a controllant tape flag attached to plants, signaling to animals such as deer and elk that the plant material is inedible. The inventive formulation also provides the advantage of the utilization of former waste whole mussels and other shellfish waste by cooking the waste and combining this material with corn oil, dry ground corn, alfalfa, or another matrix, as a safe and effective, non-toxic natural material which is non-phytotoxic, as a wildlife repellent and/or attractant. The inventive formulation is long lasting and can be applied to wet or dry plant foliage using a suitable adhesive. The formulation may also be applied to control burrowing activity of moles and other rodents.

BRIEF DESCRIPTION OF THE INVENTION

FIG. 1 shows a method of preparing the controllant formulation.

FIG. 2 shows a method of applying the controllant to a plant.

FIG. 6 shows another embodiment of a protective tree tube having controllant adhered thereto.

DETAILED DESCRIPTION OF THE INVENTION

Figure 3:
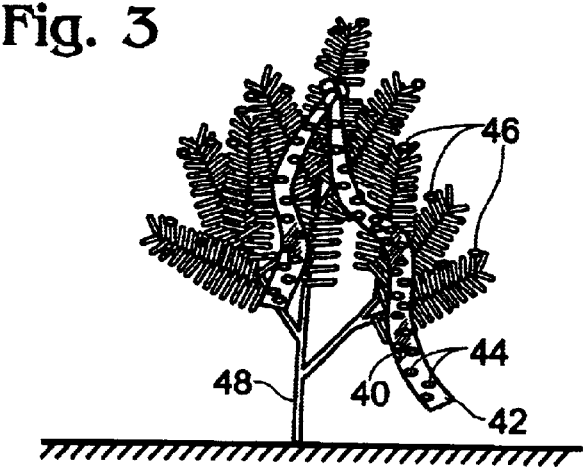
FIG. 3 shows a tree having a controllant tag secured thereto.

The inventive animal repellent and/or attractant is formulated from shellfish waste, typically including the shell and some meat or tissue of the shellfish. This shellfish waste is increasingly abundant in the significantly expanding shellfish industry and is causing an increasing waste disposal problem. The shellfish waste used for the present invention is typically taken during normal food processing operations, typically from fresh Dungeness crab (Cancer magister). However, in other embodiments the shellfish waste may comprise waste tissue and/or shell from any shellfish or mixtures thereof, including crabs, lobsters, mussels, shrimp, clams, oysters, and the like. The shells typically have been sterilized by cooking, and the tissue (meat) removed for consumption as food. In the case of mussels, however, the meat typically is included within the controllant formulation. This nearly sterile process eliminates most fats and nearly all residual protein except a small amount adhered to the shell matrix. The mineral composition of this cleaned shellfish consists primarily of calcium carbonate (about 90%, but typically greater than 80% and less than 95%) and calcium phosphate (about 10%, but typically less than 15% and more than 5%), and a limited amount of chitin (typically in a range of zero to 5%).

This cleaned shell, which is wet with processing water, is typically frozen after cleaning and held below twenty degrees Fahrenheit. To reduce the bulk of the shellfish waste material for freezer storage, it typically is chopped in a mechanical chipper before storage.

Several methods can be used to prepare waste shellfish, such as crabshell, as a dry and stable controllant formulation. The preferred method is to mix and immediately grind together (using industrial quality food mixers and grinders) the chopped frozen crabshell and a drying and/or binding agent, such as corn or granular bentonite clay (CETCO C/S Granular) at a rate of 1:1 (weight:weight), and preferably in a range of 40 to 80% crustacean shell material to 20 to 60% binder material. The clay adsorbs and absorbs most of the moisture in the shell material to facilitate rapid drying. This process appears to reduce proteolytic action and enzyme immobilization which reduces decomposition of the chitin and any residual protein. The clay also acts as a binder and a stabilizer of the shell material. Green food color (for example, Lucks Leaf Green Instant Paste Food Color or an alfalfa based colorant) is typically added while mixing to achieve the color desired to approximately match the color of the plant foliage to be treated.

Food processing type mixers and grinders produce moist extruded repellent and/or attractant material which may be immediately air dried on wire racks at room temperature, at warm outdoor temperatures on drying tables, or in ovens or over stoves at temperatures typically less than one hundred degrees Fahrenheit. In particular, the step of drying the shellfish mixture in an oven comprises reducing the water content of the mixture to a water content of less than 5 weight percent during a drying period of typically less than one hour at a temperature in a range of 80 to 100 degrees Fahrenheit. In the outdoor drying method, the method comprises reducing the water content of the mixture to a water content of less than 5 weight percent during a drying period of approximately ninety six hours. The dried, extruded material is then reground to granules approximately the size of grains of sand. Finer grinding may be required if the controllant is to be formulated in a liquid or aerosol type adhesive spray. The dry granules are then stored in closed plastic bags or similar containers at room temperature, or may be refrigerated or frozen. An alternative method is to grind, dry, and then regrind the shellfish mixture to granules without adding clay or corn, particularly if it is to be adhered to repellent tape. Of course, this procedure can be conducted with any shellfish waste, not merely just crab waste material.

In other embodiments, corn oil, corn meal, edible fish meal and alfalfa meal may each, or a combination thereof, be added to the mixture. These components each have the purpose of binding the controllant components into a matrix which slowly releases the controllant properties and provides for a granular substrate for the controllant components. Additionally, water typically also comprises a portion of the mixture wherein the water typically remains on the shellfish waste after washing and or freezing thereof.

The granular controllant is then applied to plant foliage, or other plant parts, as needed, preferably prior to a time when damage is expected. The controllant granules are adhered to plant parts with materials appropriate for the period of protection desired. Short term protection of a few days, without rainfall or irrigation, can be achieved by simply wetting the plant foliage and applying the granules by sprinkling the granules on the foliage. For up to one year of adhesion of the repellent to foliage of plants such as conifers, or shorter term adhesion to deciduous plants such as roses, adhesives such as a Bond adhesive having up to 5% solids on dry foliage may be used, or an adhesive such as Rhoplex AC-33, or Carboset 514 H, having about 10% solid adhesive material in water, can be applied to dry foliage at temperatures of about fifty degrees Fahrenheit or more. Accordingly, the adhesive may comprise water, glue, or the like, and preferably comprises a non-phytotoxic adhesive. The granules are then placed on the foliage and are adhered to the adhesive. Placement of the granules on the foliage may be accomplished by spraying, hand sprinkling of the granules, or other like methods. Good adhesion of the repellent typically requires a drying period of about two hours after application and before rainfall or irrigation.

The controllant described herein is believed to function by the release of ammonia from the shellfish waste material during the life of the controllant, when the formulation is applied to plants. In particular, the controllant, which is produced by cooking, formulating and then drying, shows efficacy because the produced controllant slowly produces ammonia as the controllant breaks down in water and sunlight after being applied to the plant foliage. This release of ammonia is believed to act as a repellent to certain animals, such as deer, elk, hares and rabbits, for example, which appear to find the ammonia emitting shellfish material unpalatable and unpleasant in smell. Due to the inventive formulation method, which is aided by the addition of the binding/drying agent, ammonia is believed to not be released from the shellfish waste material prior to application to the plant. In other words, the drying process of the present invention reduces the premature emission of ammonia from the shellfish material, thereby preserving the controllant effects of the shellfish material until the controllant is adhered to the plant or plant area desired to be protected.

The granular controllant typically will adhere when applied to foliage in wet, cool weather for up to one year when applied immediately after lightly spraying wet foliage, or during rain, with non-phytotoxic application (light or spotted) of a tree marking paint such as Nelson Aero Spot or Nelson Eco Spot. This application of paint to the foliage of conifer tree seedlings such as Douglas fir or western red cedar typically is immediately followed by the application of the crustacean/shellfish waste controllant granules. These applications can be made to coniferous tree seedlings or other plants using a bottle containing the controllant granules that is clamped to a can of spray adhesive, thereby allowing one-handed application. Moreover, application of the granules can be made either before or after planting, or during other times of the year including just after bud burst or during dormancy.

The controllant may be applied to any plants or plant areas, but in particular is believed to be effective as a controllant when applied to or around tree farm crops such as Christmas trees and nursery trees, fruit crops such as apple and pear trees, berry crops such as blackberries and raspberries, and to grain crops such as wheat or corn. Moreover, due to the non-toxic properties of the controllant, use of the controllant on food crops, such as beans, is believed to be a safe animal controllant method which allows later use of the plants for human consumption. Moreover, the controllant does not harm the plants so that use of the controllant on Christmas trees does not result in browning of the Christmas tree needles.

The embodiment comprising controllant tape may be prepared by adhering controllant granules to used Mylar computer tape, vinyl, or other materials resistant to breakdown due to adverse weather and sunlight conditions, including materials of appropriate color for animal recognition purposes. This treated tape is then tied or fastened like flags to the terminal end of controllant treated plants during initial exposure, to associate the controllant treated flags with controllant treated plants. This association causes animals such as deer and elk to subsequently believe that the foliage of untreated plants having controllant treated flags attached thereto are also treated. In other words, the controllant tape is used as a flag to signal to deer and elk that plants are unpalatable. For treatment, the tape is either sprayed or dipped in a fast drying adhesive paint and immediately treated with the controllant granules as previously described. The paint composition must be compatible with the tape surface so that the controllant adheres during the period of exposure. The same controllant treatment procedure can also be applied to plastic or mesh tubes or similar enclosure materials positioned around seedlings or other plants to protect them from animal browsing. Placement of the controllant material on the plastic or mesh tubes also reduces removal of the tubes from the seedlings by curious or browsing animals.

As an attractant, the controllant crustacean/shellfish formulation is believed to function by the release of ammonia or proteins which are an attractant material to insectivores, such as moles, and carnivores such as dogs, wolves and coyotes. Accordingly, such animals will be drawn to the controllant material such that the controllant can be used as bait to trap the animal in a traditional mechanical or cage trap. Additionally, the controllant can be used as bait to lure the animal into an area where a second material has been placed, wherein the second material adheres to the animal when the animal inspects the attractive controllant material. In this use of the controllant formulation, the controllant material typically is adhered to foliage that is placed outside the den or burrow opening. In this manner, secondary materials are adhered to the paws or fur of the unsuspecting animal which then transports the secondary material to the animal's den. The secondary material may be an odorless but harmful material that acts to harm the animal or render its burrow uninhabitable. In other words, the controllant formulation is used to entice the animal into a location for the application of the secondary material. The secondary material may comprise any material that is known to repel animals from their burrows or is otherwise used in the elimination of pests, and plays no part of the present invention.

In the case of mountain beavers and pocket gophers, the controllant material may be used as a repellent that is placed near the animal's den. In one example, the controllant material is adhered to foliage that is placed outside the animal's den. When the animal contacts the controllant treated foliage the animal will have an adverse reaction to the foliage and thereby may be reluctant to eat similar foliage desired to be protected. In this manner a sacrificial branch is used at the animal's den to discourage browsing of the plants in the near vicinity for which protection is desired.

Referring to FIG. 1, the process of producing the shellfish formulation is described. In a first step 10, the shellfish waste is provided. The shellfish waste typically is fresh but may be frozen or otherwise previously processed. The shellfish waste may comprise shell and/or tissue material from crab, lobster, mussel, shrimp, clam, oyster, and/or mixtures thereof. In step 12, the shellfish waste typically is cooked to remove most of the non-shell material, such as soft tissue/meat. However, in the case of mussels or other shellfish formulations, some or all of the tissue/meat typically will remain as a part of the shellfish waste formulation. Additionally, cooking of the shellfish may not be required in all cases. In step 14 the shellfish waste is then crushed, if required. In step 16, the cooked shell and meat material may be stored, typically in a frozen state, for as long as is required until further processing. Of course, this step may be eliminated or skipped. In step 18, the shell waste is mixed with a binding agent or agents such as clay, ground corn, corn oil and/or alfalfa. In step 20, a colorant, such as a dye or an alfalfa based colorant, may be added to the mixture to achieve a desired color, such as a color that will match a plant or excavation area to which the controllant may be applied. In step 22 the mixture is dried. This drying step typically is conducted so that the mixture does not decompose or emit ammonia during the drying process, thereby extending the useful life of the controllant when applied in the field. In step 24 the dried mixture may be further ground to desired specifications, as determined by the desired application method, such as hand sprinkling or by aerosol spraying. In step 26 the formulation is applied to the desired controllant area such as to a plant, at an excavation site, or to a substrate to be placed on a plant or at an excavation site. The controllant typically is applied in the form of a granular material to foliage after an adhesive is first applied to the foliage.

FIG. 2 shows application of the controllant formulation to a portion of a plant, namely to a leaf 30. An adhesive 32 may be first applied to the leaf, wherein the adhesive may comprise water, glue or the like. Shellfish waste formulation granules 34 are then applied to the plant and adhere on the adhesive, shown as controllant 36.

FIG. 3 shows application of the controllant to a tag which is then tied to a plant to indicate to animals that the plant is unpalatable. In particular, adhesive 40 is applied to a substrate, such as a tag 42, and the controllant 44 is then adhered to adhesive 40. Tag 42 typically comprises a flexible material that may easily be tied to the terminal end of a tree. The tag material may be treated prior to or after securement of the tag to the plant 48.

Figure 4:
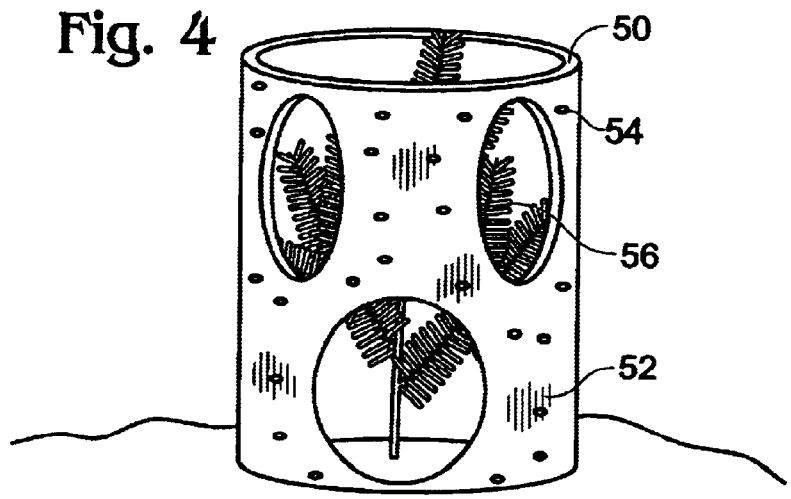
FIG. 4 shows a protective tree tube having controllant adhered thereto.

FIG. 4 shows a substrate, such as a protective tube 50, with adhesive 52 and controllant 54 adhered thereto. The substrate surrounds and therefore protects a plant 56 positioned therein.

Figure 5:
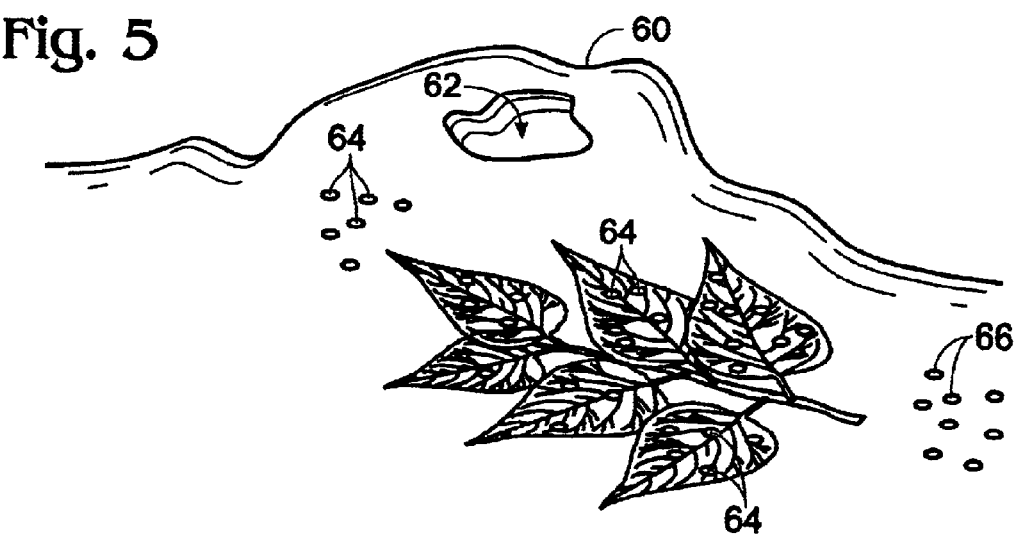
FIG. 5 shows controllant applied at an excavation site.

FIG. 5 shows an excavation mound 60 having an excavation opening 62 therein, wherein controllant 64 is placed at the excavation site to act as an attractant to excavation animals, thereby facilitating capture of the animal. The controllant may be placed directly on the ground but is preferably placed on foliage, such as twigs with leaves thereon, that is placed around the excavation entrance. In the case of an attractant, the controllant is believed to entice the burrowing animal into the area where the attractant is placed, such that a second material 66 comes into contact with the animals. The secondary material 66 may act to rid the area of the pest in a variety of ways, as known in the art.

FIG. 6 shows a second type of tree tube wherein the tube 68 comprises an open mesh. Tube 68 may have controllant 70 adhered thereto, so as to control browsing of an animal that may desire to eat or otherwise harm the plant contained within tube 68.

Turning now to a different embodiment from the crab shell embodiment disclosed above, the invention includes formulations and methods to utilize waste products or increase the utilization of waste products from the shellfish industry, specifically those waste products from the commercial processing of mussels (Mytilus galloprovincialis), for human food. The mussel shell and tissue mixture is formulated and applied as a repellent to plants needing protection from feeding injuries caused by wildlife, and as an attractant for control of damaging activities of certain mammalian insectivores.

The inventive shellfish waste formulations and methods include a variety of product formulating techniques and a variety of application techniques. Some of these approaches include: application of formulated mussel waste to the root zones of plants to repel animals such as deer, elk, hares and rabbits, and certain burrowing rodents including pocket gophers, voles, and mountain beavers, and as an attractant to protect against destructive burrowing by moles; application of the formulated mussel waste or waste extractions formulated within a liquid carrier or paint substrate to be sprayed on foliage in wet or dry weather; application of formulated mussel waste to food crops for repelling animals; application of mussel waste to protect plants against certain rodents such as mountain beavers, voles, and pocket gophers; and use as an attractant in certain formulations for control of burrowing activities of certain primarily insectivorous mammals such as moles, or as an attractant for carnivorous animals such as wolves, coyotes or dogs. In other words, the formulation including mussel waste functions in the same manner as the crab and other types of shell waste formulations described above.

This embodiment of the present invention is formulated from fresh waste whole mussel, corn oil, and ground corn. The whole mussels used typically are the mussels remaining from sorting mussels not meeting size or quality requirements for commercial sale. The fresh mussels typically are cleaned by normal commercial procedures used for preparing mussels for human consumption. The waste mussels are boiled in water for about thirty minutes, drained and cooled for about thirty minutes, then ground with a drying and/or binding agent, such as dry ground corn, at a ratio of 2:1 (weight/weight). However, a weight percentage of shellfish waste in a range of 40 to 90%, and a weight percentage of binder in a range of 10 to 60% will function to produce a controllant having the desired properties. The sterile cooked mussel typically consists of about 33% soft tissue and 66% shell (weight/weight). Approximately 7.0% corn oil (weight/weight) is added before grinding. The corn oil is added for the purpose of binding the mixture together, reducing dust during the grinding process and thereafter, and increasing the repellency of the formulation. Approximately 10% ground alfalfa or 0.002% green food color (Lucks Forest Green Food Color) is added during grinding. The ground mussel/corn oil/ground corn/food color/alfalfa formulation is immediately placed on drying screens at room temperature to evaporate off substantially all water, then reground to a granular powder. The ground corn and the ground alfalfa adsorbs and absorbs most moisture in the shell material to facilitate the drying process. This drying process appears to reduce proteolytic action and enzyme immobilization to reduce decomposition of the formulation. The granular powder is then typically weighed, placed into bags, sealed, and stored at room temperature.

The granular repellent is applied to plant foliage, or other plant parts, as needed, preferably prior to the time when damage is expected. The repellent granules are adhered to plant parts with materials appropriate for the period of protection desired. Short term protection of a few days, without rainfall or irrigation, can be achieved for food crops by simply wetting the plant foliage and applying the granules. For up to one year of adhesion of the repellent to foliage of plants such as conifers, or shorter term adhesion to deciduous plants such as roses, adhesives such as 3 to 5% solids in water Bond Spreader Sticker in (CAS No. 36208-50005) and green food color or alfalfa based colorant, in water are applied to the plant to be protected. Adhesion is best when applied to dry foliage at temperatures of about ten degrees Celsius (50 degrees Fahrenheit) or higher. The controllant formulation is then sprinkled or sprayed on the adhesive which is on the plants. Good adhesion of the repellent requires a drying period of about two hours after application before rainfall or irrigation.

The granular repellent will adhere when applied to foliage in wet, cool weather for up to one year when applied immediately after lightly spraying wet foliage, or during rain, with non-phytotoxic application (light or spotted) of tree marking paint such as Nelson Aero Spot or Nelson Eco Spot. The paint is applied to the foliage of conifer tree seedlings such as Douglas fir or western red cedar immediately followed by the application of repellent granules. These applications can be made to coniferous tree seedlings or other plants using a repellent bottle containing granules that is clamped to a can of spray adhesive, allowing one-handed application, either before or after planting, or during other times of the year including just after bud burst or during dormancy.

In this embodiment, controllant tape is prepared by adhering controllant granules to plastic or vinyl tape or flagging, or similar weather and sunlight resistant materials. The controllant treated tape is fastened to the tops of controllant treated plants. This facilitates association of the controllant treated flags with controllant treated plants. This causes deer and elk to subsequently believe that the foliage of untreated plants with controllant treated flags are also treated. For treatment the tape is either sprayed or dipped in an adhesive and immediately treated with the controllant granules, as previously described. The same controllant treatment procedure can also be applied to plastic mesh tubes or similar materials applied to protect tree seedling or other plants.

A specific example of one formulation method is set forth as follows. A batch of controllant material is prepared having a total, fresh, wet weight of 6420 grams. This total weight includes 4000 grams of fresh whole mussels. The mussels have been boiled for 20 to 30 minutes, drained, and then cooled. The mussels contain about 45% water. The formulation also contains 500 grams of alfalfa, 1500 grams of dry ground corn and 420 grams of corn oil. Accordingly, in this example, the corn oil is approximately 7% of the total fresh wet weight of the formulation. The corn oil is added to the whole mussels and the mixture is then crushed in a commercial mixer. The alfalfa is then added to the above mixture. The ground corn is then added to the above mixture and the mixture is mixed for five minutes. The moist mixture is then passed through a commercial grinder with a ¼ inch die. The ground mixture is then spread on $\frac{1}{16}^{th}$ to $\frac{1}{8}^{th}$ inch screens for drying. Using fans, the mixture is air dried at room temperature, at approximately 50 to 80 degrees Fahrenheit, for about 96 hours. When the mixture is dry, defined as including approximately less than 5% water, the formulation is reground as described above to form a granular powder. The granular powder is then packaged in airtight plastic containers and labeled. The dry weight of the final formulation was 4619 grams. The water loss from the mussel was approximately 45.02%. The water loss from the total mixture during the drying process was approximately 28.05%.

Based on this dry weight of the final formulation, the corn oil is 420 grams of the total 4619 grams, and therefore is approximately 9.09% of the dry formulation. As stated above, the corn oil has a controllant function caused by rancidity when the formulation is exposed to air. The corn oil also acts as a binder, a dust control agent, improves the flow of the dry formulation, and provides some adhesive properties. The ground alfalfa is 500 grams of the total 4619 grams, and therefore is approximately 10.82% of the dry formulation. The alfalfa acts as a colorant, a binder and an extender of the life of the formulation. The ground corn is 1500 grams of the total 4619 grams, and therefore is approximately 32.47% of the dry formulation. The ground corn acts as a binder, an extender, and has similar properties to the corn oil. The ground mussel is 2199 grams of the total 4619 grams and therefore is approximately 47.60% of the dry formulation. The ground mussel acts as a controllant due to its odor, taste and physical texture. In particular, the shell porosity of the mussel acts to slowly release decomposing proteins and ammonia. The mussel material also acts as a binder.

In the example of crab shell and waste shrimp shell embodiments, these shells normally have been cooked prior to receipt at the shellfish waste processing facility. Additionally, most of the meat has been removed. The crab or shrimp waste typically is kept cool, or frozen, and then processed as in the above listed example. The hard crab shell typically must be ground in a coarse grinder before being mixed in the ¼ inch grinder. However, shrimp shell waste is generally softer and is easily ground in the ¼ inch grinder.

The crab and/or shrimp formulation typically is processed in a similar fashion as the mussel example give above, and then packaged in airtight plastic containers and stored at room temperature.

While preferred embodiments of the present invention have been shown and described, it will be apparent to those skilled in the art that many changes and modifications may be made without departing from the invention in its broader aspects. The appended claims are intended to cover, therefore, all such changes and modifications as fall within the true spirit and scope of the invention.

We claim:

1. An animal repellent, comprising:

ground shellfish waste material, and a binder material, wherein said ground shellfish waste material comprises a weight percentage of the repellent in a range of 40 to 90 percent, and wherein said repellent is adhered to a substrate manufactured of plastic.

2. An animal repellent, comprising:

shellfish waste material comprising a weight percentage of the repellent in a range of 40 to 90 percent, and wherein said shellfish waste material comprises mussel material comprising soft mussel tissue in range of 20 to 40 weight percent of the shellfish waste material and ground hard mussel shell in a range of 40 to 80 weight percent of the shellfish waste material, a binder material comprising ground corn, corn oil in a range of 5 to 10 weight percent of the repellent, and colorant in a range of 0.001 to 10 weight percent of the repellent.

* * * * *